United States Patent [19]

Salerno

[11] Patent Number: 6,150,500
[45] Date of Patent: Nov. 21, 2000

[54] ACTIVATORS OF ENDOTHELIAL NITRIC OXIDE SYNTHASE

[76] Inventor: John C. Salerno, 8 Lansing Ave., Troy, N.Y. 12180

[21] Appl. No.: 08/679,006

[22] Filed: Jul. 12, 1996

[51] Int. Cl.[7] .................................................. A61K 38/00
[52] U.S. Cl. ......................... 530/300; 530/326; 530/327; 530/387.1; 530/387.9; 530/388.2; 530/388.26
[58] Field of Search ................................ 530/300, 388.1, 530/326, 327, 387.1, 387.9, 388.2, 388.26

[56] References Cited

U.S. PATENT DOCUMENTS

| | | | |
|---|---|---|---|
| 5,268,465 | 12/1993 | Bredt et al. | 435/252.3 |
| 5,498,539 | 3/1996 | Harrison et al. | 435/240.2 |

FOREIGN PATENT DOCUMENTS

| | | |
|---|---|---|
| 9318156 | 9/1993 | WIPO. |
| 9412645 | 6/1994 | WIPO. |

OTHER PUBLICATIONS

Jarrett, H., et al., "Calmodulin–binding Proteins Also Have a Calmodulin–like Binding Site within Their Structure," *The Journal of Biological Chemistry*, 266(1): 362–371 (Jan. 5, 1991).

Moncada, S., et al., "Endogenous nitric oxide: physiology, pathology and clinical relevance," *European Journal of Clinical Investigation*, 21: 361–374 (1991).

Brickey, D., et al., "Mutational Analysis of the Autoinhibitory Domain of Calmodulin Kinase II," *The Journal of Biological Chemistry*, 269(46): 29047–29054 (Nov. 18, 1994).

Nishimura, J., et al., "Modular Structure of Neuronal Nitric Oxide Synthase: Localization of the Arginine Binding Site and Modulation by Pterin," *Biochemical and Biophysical Research Communications*, 210(2): 228–294 (May 16, 1995).

Venema, R., et al., "Identification, Characterization, and Comparison of the Calmodulin–binding Domains of the Endothelial and Inducible Nitric Oxide Syntases," *The Journal of Biological Chemistry*, 271(11): 6435–6440 (Mar. 15, 1996).

Madison, D., et al., "Pass the Nitric Oxide," *Proc. Natl. Acad. Sci, USA*, 90: 4329–4331 (May, 1993).

Garvey, E., et al., "Potent and Selective Inhibition of Human Nitric Oxide Synthases," *The Journal of Biological Chemistry*, 269(43): 26669–26676 (Oct. 28, 1994).

Ignarro, L., et al., "Endothelium–derived relaxing factor produced and released from artery and vein is nitric oxide," *Proc. Natl. Acad. Sci. USA*, 84: 9265–9269 (1987).

Nathan, C., et al., "Role of nitric oxide synthesis in macrophage antimcrobial activity," *Current Opinion in Immunology*, 3: 65–70 (1991).

Ignarro, L., et al., "Nitric Oxide and Cyclic GMP Formation Upon Electrical Field Stimulation Cause Relaxation of Corpus Cavernosum Smooth Muscle," *Biochemical and Biophysical Research Communications*, 170(2): 843–850 (Jul. 31, 1990).

Abu–Soud, H., et al., "Nitric oxide synthases reveal a role for calmodulin in controlling electron transfer," *Proc. Natl. Acad. Sci. USA*, 90: 10769–10772 (Nov. 1993).

Lowenstein, C. and Snyder, S., "Nitric Oxide, A Novel Biologic Messenger," *Cell*, 70: 705–707 (Sep. 4, 1992).

Green, I., et al., "Effects of cytokines and nitric oxide donors on insulin secretion, cyclic GMP and DNA damage: relation to nitric oxide production," *Biochemical Society Transactions*, 22: 30–36 (1994).

Bredt, D., et al., "Cloned and expressed nitric oxide synthase structurally resembles cytochrome P–450 reductase," *Nature*, 351: 714–718 (Jun. 27, 1991).

Janssens, S., et al., "Cloning and Expression of a cDNA Encoding Human Endothelium–derived Relaxing Factor/Nitric Oxide Synthase," *The American Society for Biochemistry and Molecular Biology, Inc.*, 267(21): 14519–14522 (Jul. 25, 1991).

Lamas, S., et al., "Endothelial nitric oxide synthase: Molecular cloning and characterization of a distinct constitutive enzyme isoform," *Proc. Natl. Acad. Sci. USA*, 89: 6348–6352 (Jul. 1992).

Xie, Q., et al., "Cloning and Characterization of Inductible Nitric Oxide Synthase from Mouse Macrophages," *Science*, 256: 225–228 (Apr. 10, 1992).

Lowenstein, C., et al., "Cloned and expressed macrophage nitric oxide synthase contrasts with the brain enzyme," *Proc. Natl. Acad. Sci. USA*, 89: 6711–6715 (Aug. 1992).

Marletta, M., "Nitric Oxide Synthase: Aspects Concerning Structure and Catalysis," *Cell*, 78: 927–930 (Sep. 23, 1994).

Lyons, C., et al, "Molecular Cloning and Functional Expression of an Inducible Nitric Oxide Synthase form a Murine Macrophage Cell Line," *The Journal of Biological Chemistry* 267(9): 6370–6374 (Mar. 28, 1992).

Nathan, C., et al., "Nitric Oxide Synthases: Roles, Tolls, and Controls," *Cell*, 78: 915–918 (Sep. 23, 1994).

Schmidt, H., et al., "NO at Work," *Cell*, 78: 919–925 (Sep. 23, 1994).

(List continued on next page.)

*Primary Examiner*—Paula K. Hutzell
*Assistant Examiner*—Susan Ungar
*Attorney, Agent, or Firm*—Hamilton Brook Smith & Reynolds, P.C.

[57] ABSTRACT

The regulatory peptides for constitutive nitric oxide synthase enzymes, and a peptide specific to inducible nitric oxide synthase, as well as derivatives of the peptides, homologous peptides, nucleic acids encoding the peptides, derivatives, and homologous peptides, and antibodies to the peptides, derivatives, and homologous peptides, are disclosed. The peptides, derivatives, homologous peptides, antibodies, and nucleic acids, as well as peptidomimetics, can be used in methods of modulating the activity of nitric oxide synthase enzymes, and also in methods of treating diseases or conditions modulated by production of nitric oxide by nitric oxide synthases. Assays for identifying agents which modulate the activity of the nitric oxide synthase enzymes are also described.

6 Claims, 1 Drawing Sheet

OTHER PUBLICATIONS

Stamler, J., "Redox Signaling: Nitrosylation and Related Target Interactions of Nitric Oxide," *Cell,* 78: 931–936 (Sep. 23, 1994).

Palacios, Miriam et al., "Chlorpromazine Inhibits Both the Constitutive Nitric Oxide Synthase and the Induction of Nitric Oxide Synthase After LPS Challenge," *Biochemical and Biophysical Reserach Communications,* 196(1): 280–286 (1993).

Wolff, Donald J. et al., "Calmodulin–dependent Nitric–oxide Synthase," *Journal of Biological Chemistry,* 268(13):9425–9429 (1993).

Nakane, Masaki et al., "Novel Potent and Selective Inhibitors of Inducible Nitric Oxide Synthase," *Molecular Pharmacology,* 47(4): 831–834 (1995).

Watanabe, Yasuo et al., "Identification of a specific amino acid cluster in the calmodulin–binding domain of the neuronal nitric oxide synthase," *FEBS Letters,* 403(1): 75–78 (1997).

Mayer, Bernd et al., "A Synthetic Peptide Corresponding to the Putative Dihydrofolate Reductase Domain of Nitric Oxide Synthase Inhibits Uncoupled NADPH Oxidation," *Nitric Oxide,* 1(1):50–55 (1997).

Burgess et al. (J. Cell Bio, 111:2129–2138, 1990).

Tao et al (J. Immunol, 143: 2595–2601, 1989).

Lazar et al (Mol & Cell Bio., 8:1247–1252, (1988).

Wood et al (BBRC, 191:767–774, 1993).

Xue et al (J. Autonomic Nervous System, 49: 1–14, 1994).

FIGURE

```
                                             INITIAL FMN BINDING REGION
NCPR_HUMAN   ESSFVEKMKK   TGRNIIVFYG   SQTGTAEEFA   NRLSKD.AHR   YGMRGMSADP   115
NOSE_BOVIN   GTLMAKRV..   ...KATILYA   SETGRAQSYA   QQLGRLFRKA   FDPRVLCMD.   556
NOSB_RAT     GQAMAKRV..   ...KATILYA   TETGKSQAYA   KTLCEIFKHA   FDAKAMSME.   789
NOSM_MOUSE   RKVMASRV..   ...RATVLFA   TETGKSEALA   RDLATLFSYA   FNTKVVCMD.   567
FLAV_ECOLI   ........ .   .AITGIFFG    SDTGNTENIA   KMIQKQL.GK   .D.VADVHDI   35
FLAV_DESVH   ........ .   .MPKALIVYG   STTGNTEYTA   ETIARELADA   .GYEVDSRDA   38

FLANKING LOOP                         SECOND FMN SITE
NCPR_HUMAN   EEYDLADLSS   LPEIDNALVV   FCMATYGEGD   PTDNAQDFYD   WL.QE.....   159
NOSE_BOVIN   .EYDVVSL..   ...EHETLVL   VVTSTFGNGD   PPENGESFAA   AL.MEMSGPY   599
NOSB_RAT     .EYDIVHL..   ...EHEAIVL   VVTSTFGNGD   PPENGEKFGC   AL.MEMRHP.   831
NOSM_MOUSE   .QYKASTL..   ...EEEQLLL   VVTSTFGNGD   CPSNGQTLKK   SLFML.....   606
FLAV_ECOLI   AKSSKEDL..   ...EAYDILL   LGIPTWYYGE   ...AQCDWD    DF.FP.....   70
FLAV_DESVH   ASVEAGGLF    ...EGFDLVL   LGCSTWGDDS   IE..LQDDFI   PL.FD.....   76

LOCATION OF REGULATORY LOOP INSERT
NCPR_HUMAN   ..........   ..........   ..........   RKRKESSNTD   TDVDLSGVKF   169
NOSE_BOVIN   NSSPRPEQHK   SYKIRFNSVS   CSDPLVSSWR   ..........   SAGAGTLRFL   649
NOSB_RAT     NS..VQEERK   SYKVRFNSVS   SYSDSRKSSG   DGPDLRDNFE   STGPLANVRF   879
NOSM_MOUSE   ..........   ..........   ..........   ..........   .RELNHTFRY   615
FLAV_ECOLI   ..........   ..........   ..........   ........TL   EEIDFNGKLV   82
FLAV_DESVH   ..........   ..........   ..........   ........SL   EETGAQGRKV   88

THIRD FMN SITE   FLANKING LOOP
NCPR_HUMAN   AVFGLGNKT.   Y.EHFNAMGK   YVDKRLEQLG   AQRI   201
NOSE_BOVIN   CVFGLGSRA.   Y.PHFCAFA.   AVDTRLEELG   GERL   680
NOSB_RAT     SVFGLGSRA.   Y.PHFCAFGH   AVDTLLEELG   GERI   911
NOSM_MOUSE   AVFGLGSSM.   Y.PQFCAFAH   DIDQKLSHLG   ASQL   647
FLAV_ECOLI   ALFGCGDQED   YAEYFCDALG   TIRDIIEPRG   ATIV   116
FLAV_DESVH   ACFGCGDSS.   Y.EYFCGAVD   AIEEKLKNLG   AEIV   120
```

ACTIVATORS OF ENDOTHELIAL NITRIC OXIDE SYNTHASE

BACKGROUND OF THE INVENTION

Nitric oxide (NO), a small molecule which is highly toxic at moderate concentrations, is a key messenger in mammalian physiology. NO is produced in humans by three related enzymes which comprise the nitric oxide synthase (NOS) family.

Endothelial NOS (ENOS) produces NO which controls vascular tone (hence blood pressure), dilates the airways, and controls numerous processes dependent on local dilation of blood vessels (such as gas exchange in lungs, penile erection, and renal function). Brain or neuronal NOS (BNOS or NNOS) produces NO which functions as a neurotransmitter. It controls peristalsis in the gut, and is implicated in neural potentiation and brain development. NNOS and ENOS are constitutive enzymes controlled by intracellular calcium and the regulatory protein calmodulin (CAM). When the level of calcium in the cell rises, NNOS and ENOS bind calmodulin and are turned on to start NO production.

A third, inducible NOS, immune NOS or macrophage NOS (INOS or MNOS), is synthesized by the immune system in response to an immune challenge. Upon induced expression, this enzyme is always active; it has a calmodulin binding site, but binds calmodulin tightly even at low calcium levels. INOS produces orders of magnitude more NO than other NO synthases. This NO level is cytotoxic to tumor cells, bacteria, and other pathogenic organisms.

While INOS thus appears to be an important component of immune response, its activity is highly toxic as well. Excess production of NO by INOS can be responsible for toxic shock syndrome, septic shock, and killing of islet cells in diabetes. Excess NO production by INOS has also been implicated in a wide range of other autoimmune conditions, including arthritis and other inflammatory conditions.

Thus, it is of critical importance to learn to control NO synthesis by one NOS, without interfering with the activity of other NO synthases. Currently, inhibitors of INOS also inhibit NNOS and ENOS.

SUMMARY OF THE INVENTION

The current invention concerns recently discovered intrinsic control site elements of constitutive nitric oxide synthases. These intrinsic control site elements, referred to as "regulatory peptides," include the regulatory peptide of endothelial nitric oxide synthase (ENOS), MSGPYNSSPRPEQHKSYKIRFNSVSCSDPLVSSWRRKRKESSNTD (SEQ. ID. NO. 1); the regulatory peptide of neuronal nitric oxide synthase (NNOS) MRHPNSVQEERKSYKVRFNSVSSYSDSRKSSGDGPDLLRDNFE (SEQ. ID. NO. 2); a polypeptide specific to inducible nitric acid synthase (INOS), SEQUENCE (SEQ. ID. NO. 3). Based on this discovery, methods are now available to identify agents that modulate (activate or inhibit) NOS activity, as well as the agents themselves. Agents include agents that inhibit NOS activity by blocking calmodulin activation of the NOS enzyme; agents that inhibit NOS activity by blocking electron transfer from NADPH to an active site in NOS; agents that activate a constitutive NOS enzyme by antagonizing autoinhibition of a regulatory region of the NOS enzyme; and agents that modulate NOS activity by interacting with the regulatory peptide or spatially adjacent control regions. The agents include the peptides described above, as well as derivatives of these peptides, and homologous peptides. Homologous peptides include substantially isolated peptides having an array of at least two positively charged amino acids, and an amino acid sequence of at least about 60% homology, or about 67% homology, or about 80% homology, or about 90% homology, to the amino acid sequence of the ENOS regulatory peptide; peptides having an amino acid sequence of at least about 60% homology, or about 67% homology, or about 80% homology, or about 90% homology, to the amino acid sequence of the NNOS regulatory peptide; peptides having an amino acid sequence of at least about 60% homology, or about 67% homology, or about 80% homology, or about 90% homology, to the amino acid sequence of the INOS-specific peptide; and peptides having an amino acid sequence of at least about 60% homology, or about 67% homology, or about 80% homology, or about 90% homology, to the amino acid sequence of the negatively charged loops of the NOS enzymes. The invention further concerns nucleic acids encoding the peptides, derivatives, and homologous peptides; fusions of peptides with proteins or other macromolecules (e.g., polysaccharides); peptidomimetics of the peptides, derivatives, and homologous peptides; and antibodies (either monoclonal or polyclonal antibodies, or fragments thereof) to the peptides, derivatives, and homologous peptides.

The agents can be used to modulate the activity of NOS enzymes. Preferably, the agents modulate the activity of one NOS enzyme, but do not substantially affect the activity of the other NOS enzymes. Such agents can be used to treat diseases or conditions mediated by production of nitric oxide by inducible nitric oxide synthase, such as toxic shock, septic shock, autoimmune diseases, inflammatory conditions, and diabetes. The agents can also be used to treat diseases or conditions mediated by production of nitric oxide by a constitutive NOS enzyme, such as hypertension, diabetes, or AIDS-related dementia.

Thus, as a result of the discovery described herein, it is now possible, for the first time, to design and/or isolate isoform-specific inhibitors, and also isoform-specific activators, of the different NOS isoforms. This overcomes the limitations of earlier methods, which restricted drug discovery to analogs of substrates, such as arginine, or cofactors, such as tetrahydrobiopterin. Furthermore, the current discovery allows identification of activators of NOS enzymes, which was previously impossible.

BRIEF DESCRIPTION OF THE FIGURE

The FIGURE demonstrates the alignment of a selected set of NOS, cytochrome P450 reductase (CPR), and bacterial flavodoxin sequences, illustrating the conservation of regions involved in FMN binding.

DETAILED DESCRIPTION OF THE INVENTION

The current invention pertains to the discovery of the existence and identity of regulatory peptides of constitutive nitric oxide synthase (NOS) enzymes. As described in the Examples below, Applicant has identified the regulatory peptide of constitutive NOS enzymes as an intrinsic polypeptide insert in the flavin mononucleotide (FMN) binding domain of endothelial nitric oxide synthase (ENOS), MSGPYNSSPRPEQHKSYKIRFNSVSCSDPLVSSWRRKRKESSNTD (SEQ. ID. NO. 1) and in brain or neuronal nitric oxide synthase (NNOS) MRHPNSVQEERKSYKVRFNSVSSYSDSRKSSGDGPDLLRDNFE (SEQ. ID. NO. 2). Inducible nitric oxide synthase (INOS) lacks a similar polypeptide insert; instead, INOS has an INOS-specific region (the "INOS-specific polypeptide"), amino acids 600–615 of INOS (SEQ. ID. NO. 3), a short loop which is split and greatly extended by the introduction of the regulatory peptide (also referred to herein as the intrinsic peptide) in ENOS and NNOS. Applicant has also identified a core region of the ENOS binding domain: the array of positively charged amino acids, RRKRK (SEQ ID NO. 7), within the ENOS binding domain, alters activity of the enzyme.

As a result of the discovery, methods are now available for isolating or identifying an entirely new class of NOS isoform-specific inhibitors or activators. As disclosed herein, it is now possible to design and/or screen for agents which modulate (either inhibit or activate) a specific isoform of NOS, without altering the activity of other isoforms. The invention includes both the methods by which agents can be isolated or identified, as well as those agents so isolated and identified.

Agents of the invention include agents that modulate, and particularly inhibit, nitric oxide synthase activity by, for example, blocking activation of the NOS by calmodulin. The agents also include agents that modulate, and particularly activate, a constitutive NOS by, for example, antagonizing or interfering with autoinhibition of the enzyme by a regulatory region of the enzyme, as described herein. The agents also include agents which bind to sites spatially adjacent to the calmodulin binding site of a constitutive NOS enzyme. The agents further include agents that inhibit NOS by blocking electron transfer from NADPH to an active site in NOS. Representative agents include certain substantially isolated peptides, including the regulatory peptides of ENOS and NNOS, the INOS-specific peptide, the negatively charged loops of INOS, ENOS and NNOS, as well as derivatives of the peptides and homologous peptides. Nucleic acids encoding the peptides, derivatives and homologous peptides are also available, as are antibodies specific to the peptides, their derivatives and homologs. Agents which bind to these peptides, as well as agents that bind to the control regions of the NOS isoforms, and agents which bind to functional groups within the INOS-specific peptide, are also agents of the invention. In addition, methods of altering the activity of ENOS, NNOS, or INOS; methods of treating diseases mediated by production of nitric oxide; methods of treating conditions mediated by ENOS; and methods of treating conditions mediated by NNOS, are available. The methods include use or administration of the agents described herein.

The discussion below presents screening methods for agents that modulate NOS enzymes; screening methods for agents that inhibit INOS; screening methods for agents that activate constitutive NOS enzymes; preparation and design of agents that bind to control sites for NOS isoforms; peptides, probes, nucleic acids, and antibodies of the invention; and uses of agents, peptides, and antibodies of the invention, including methods of treatment of certain diseases or conditions associated with NO production in mammals, including humans.

General Screening Methods for Agents that Modulate NOS Activity

Based on the discovery of the regulatory regions of NOS isoforms, it is now possible to identify agents which modulate the activity of a nitric oxide synthase. An agent which "modulates" the activity of a nitric oxide synthase, as used herein, is an agent which either increases or decreases the activity of an NOS enzyme. Agents which increase the activity of an NOS enzyme are those which activate or promote the activity of the NOS enzyme. Agents which decrease the activity of an NOS enzyme are those which inactivate, interfere with, minimize or prevent the activity of the enzyme. Agents of the invention can modulate NOS enzyme activity independently of calmodulin activation of the NOS enzyme; that is, whether or not calmodulin is associated with the NOS enzyme, it is the agent, rather than the calmodulin, that activates the NOS enzyme.

Current screening strategies for agents that modulate NOS activity are limited to methods that screen for agents that inhibit NOS enzyme activity. Screening methods for arginine (and pterin) analog inhibitors depend upon assays which are designed to define the effect on activity of the occupation of substrate (arginine) and/or cofactor (e.g., tetrahydrobiopterin). Conditions are selected to ensure that the limitation on enzyme activity is imposed at the catalytic site, and on arginine and N-OH arginine hydroxylation per se rather than on the preceding electron transfer reactions. A screen for an arginine analog NOS inhibitor includes arginine concentrations high enough to produce good activity for an extended time course in the absence of inhibition, but preferably not so high that strong inhibitors would be outcompeted by substrate for the binding site. All other conditions are adjusted to produce maximal or nearly maximal activity; the pterin binding site is saturated, and excess levels of calcium and calmodulin are included so that the arginine site occupancy fraction, and not electron transfer from NADPH, is rate limiting. The strategy for screening for a pterin based inhibitor is similar, except that the arginine concentration is preferably saturating, and the enzyme is preferably pretreated with pterin analogs to be screened because of the slow "off rate" of tetrahydrobiopterin. This can be accomplished with pterin replete enzyme by a long (e.g., one or more hours) preincubation with potential inhibitors, or with pterin free recombinant enzyme by a short (e.g., less than one hour) preincubation followed by reconstitution with tetrahydrobiopterin.

In contrast to these methods, screens for inhibitory agents that interact with the newly-identified regulatory regions of the NOS isoforms differ in that conditions are preferably chosen so that the rate limitation is imposed on the controlled steps, which are electron transfer reactions in which reduction of the catalytic heme group by NADPH is mediated by FMN and FAD. Conditions are selected so that the enzyme is replete with all cofactors and arginine, oxygen and NADPH are far above their Kd values for a sufficient time course to observe good kinetics. For inhibitor selection, NADPH consumption can be measured, as it is easier to measure than NO or citrulline production. If NADPH consumption is inhibited, NO and citrulline production must also be inhibited; however, the converse is not true, since under some conditions NADPH to oxygen electron transfer can be uncoupled from electron transfer.

The most important difference is the selection of calcium and calmodulin concentrations so that nearly maximal activity is obtained in the absence of the potential inhibitors, but also so that the control site is not supersaturated with $CA^{2+}$—CAM. The excess levels of calcium and calmodulin (CAM) used in standard NOS assays to ensure complete activation are sufficient to mask the effects of fairly potent control site peptide inhibitors, because the binding domains of these inhibitors overlap that of $Ca^{2+}$—CAM, leading to competitive binding. The discovery of the regulatory regions, and the description of some of the properties of the regulatory regions and the related control sites of the NOS isoforms, as described herein, make it possible to select criteria to identify agents which interact with the newly identified active sites. Prior to the discovery of the regulatory regions of NOS enzymes, there was no theoretical basis to expect that such agents existed or could be isolated.

Bearing in mind these considerations, assays can be used to determine whether an agent modulates NOS activity. A sample of the agent to be tested (the "test agent") is contacted with a sample of NOS (thereby generating a test sample, herein referred to as a "synthase sample"); after incubation of the synthase sample under conditions appropriate for activity of the enzyme, as described above, the level of NOS activity is measured. The level of NOS enzyme activity can be, for example, compared to the amount of activity of a control sample of the NOS under the same conditions but in the absence of the test agent. The level of INOS activity, or of the constitutive NOS enzyme activity, is measured by any one of several methods; the choice of method depends on the intent of the assay, as described above. If the level of activity in the synthase test sample is different from the level of activity of a control sample of the NOS under the same conditions but in the absence of the test agent, then the agent modulates the activity of the NOS.

Similarly, assays can be used to determine whether an agent modulates the activity of one NOS isoform without modulating the activity of other NOS isoforms. For example, an agent can be assayed to test whether it modulates the activity of INOS, without modulating the activity of a constitutive NOS enzyme. A sample of the agent to be tested (the "test agent"), such as an antibody, peptide, or peptidomimetic described above, is contacted with a sample of INOS (thereby generating a test sample, herein referred to as a "inducible synthase sample"); after incubation of the inducible synthase sample under conditions appropriate for activity of the enzyme, the level of INOS activity is measured. The level of INOS enzyme activity can be, for example, compared to the amount of activity of a control sample, of INOS under the same conditions but in the absence of the test agent. Similarly, a sample of the constitutive NOS enzyme is contacted with the test agent, to form a second test sample (herein referred to as the "constitutive synthase sample") after incubation of the constitutive synthase sample under conditions appropriate for activity of the enzyme, the level of activity in the constitutive synthase sample is measured, and compared with the level of activity in a sample of the same constitutive NOS enzyme, under the same conditions, without the test agent. The level of INOS activity, or of the constitutive NOS enzyme activity, is measured by any one of several methods; the choice of method depends on the intent of the assay, as described above.

If the level of activity in the inducible synthase test sample is different from the level of activity of a control sample of INOS under the same conditions but in the absence of the test agent, and if the level of activity in the constitutive synthase test sample is approximately equal to the level of activity of a control sample of the constitutive NOS under the same conditions but in the absence of the test agent, then the agent modulates the activity of INOS, but does not modulate the activity of the constitutive NOS. Conversely, if the level of activity in the constitutive synthase test sample is different from the level of activity of a control sample of the constitutive NOS under the same conditions but in the absence of the test agent, and if the level of activity in the inducible synthase test sample is approximately equal to the level of activity of a control sample of INOS under the same conditions but in the absence of the test agent, then the agent modulates the activity of the constitutive NOS enzyme, and does not modulate the activity of INOS.

The selection of inhibitors with isoform specific properties involves comparison of inhibitory effects among assays involving all three isoforms. Such assays are performed as described above, using a test and a control sample for each NOS enzyme. In selecting for NNOS or ENOS specific inhibitors, screens devised as described above are set up for NNOS and ENOS with the aim of selecting compounds which are significantly more potent inhibitors of one isoform than the other. An agent that "specifically inhibits" a particular NOS enzyme is an agent that inhibits that NOS isoform activity by approximately tenfold.

Screening Methods for Agents that Specifically Inhibit INOS

Because INOS lacks an analog of the autoinhibitory element of ENOS and NNOS, and is much stronger binder of CAM; INOS binding of CAM is almost irreversible. Thus, during assays to identify agents that modulate INOS activity, excess CAM is not added: because in order to express active INOS, CAM must be coexpressed, and INOS is isolated replete with its CAM complement. INOS retains a site of interaction for inhibitory peptides, but because of the effectively zero off rate for CAM these peptides must bind to the INOS-CAM complex. Screens set up for assays of INOS which are analogous to the ENOS and NNOS assays mentioned above, except for the omission of added calcium and CAM, detect inhibitors which can form a ternary complex with INOS and CAM but not inhibitors which are strictly competitive with CAM. Strategies for an INOS screen which would detect inhibitors competitive with CAM include co-expression of a series of peptide inhibitors with INOS and CAM, or production of INOS in the presence of the inhibitor. This provides the opportunity for tight binding inhibitors to bind to the enzyme before CAM blocked their recognition site.

Additional Methods for Design and/or Identification of Agents that Inhibit Specific NOS Isoforms NOS specific inhibitors can also be identified by using neighboring structural elements of the control site to design and screen for agents that interact with the control site. These elements in INOS include the short connecting loop that is specific to inducible nitric acid synthase (SEQ ID NO. 3), which occupies the position of the extended constitutive NOS insertion in the FMN domain, and the two flanking, negatively charged, loop sequences which correspond to the helix-strand transitions in INOS. An agent that binds to the loop that is specific to inducible NOS (SEQ ID NO. 3) occupies a position in INOS that is analogous to that of the regulatory element in constitutive NOS, and hence has potential inhibitory character. Agents that bind to the flanking loops can have binding domains which overlap the binding domain for the regulatory element, and can be inhibitory.

Similarly, alternative control site inhibitors for ENOS and NNOS have also been identified. Agents that bind to the corresponding flanking loop sequences in those isoforms can also serve as inhibitors. Such agents are now available. As described below, peptides corresponding to all the control site elements, both regulatory and structural, have been synthesized; antibodies to these peptides are examples of agents described above. Other agents can be identified by using a charge complement strategy; by screening an appropriate peptide library using an INOS inhibition assay; or by screening an appropriate peptide library using a selection strategy involving assaying for binding to the peptides.

Screening Methods for Agents that Activate ENOS and NNOS

Prior to the discovery of the regulatory region of the NOS isoforms, as described herein, it was not known that NOS activation was possible by any means other than by CAM activation of the enzyme. Activation of constitutive NOS enzymes is particularly desirable, for treatment of diseases and conditions associated with NO production. Activation of ENOS and NNOS can most readily be visualized in terms of an agent that binds to the regulatory element of the isoform of interest, so as to prevent autoinhibition of NOS. An example of such an agent is an antibody to the regulatory element, which serves to interfere with the inhibited conformation. Other agents that bind to the regulatory element can be designed or identified by screening for activation. Design of agents utilizes charge complementarity: since a critical feature of the regulatory elements is the presence of an array of predominantly positive charges, activator candidates have arrays of predominantly negative charges. Since extension of peptides containing positive charge arrays with additional residues corresponding to ENOS and NNOS regulatory elements which contain a few, or one negative charge, produce inhibitors of lower Kd than the positive charge array alone, flanking regions bearing one, or a few positive charges around a core of negative charges may be more potent as binding agents, and hence as activators.

The flanking loop sequences of all three NOS isoforms bear negative charges. In addition for their importance as sites for directed binding with regulatory potential, in constitutive NOS these sequences are part of the binding domain, and possibly part of the recognition site, of the regulatory peptide. In INOS, the corresponding sequences occupy the analogous positions spatially adjacent to the vestigial regulatory site. Structurally, the constitutive NOS flanking loops form the edges of a cup which surrounds the base of the regulatory peptide. This suggests that the negative charges on these loops may interact with some of the positive charges on the regulatory peptide, and hence the synthetic peptides derived from these loops are examples of the agents bearing negative charge arrays discussed above. Thus, they are potentially CAM independent activators.

Screens for CAM independent control site activation of a NOS enzyme uses assays in which conditions are selected for nearly maximum activity, except that no CAM is added. This includes saturation of the enzyme with arginine, oxygen and NADPH, and, if necessary, reconstitution with tetrahydrobiopterin. Potential activators are selected for their ability to stimulate NO production. While it is possible to use NADPH consumption as an initial assay for this screen, it is preferable to use NO (or citrulline) formation as a basis for the assay, as an increase in NADPH consumption could be due to an increase in the uncoupled rate of electron transfer to oxygen.

Design of Agents That Bind to Control Sites of NOS Isoforms

Based on the discovery of the regulatory region of the NOS isoforms, agents that bind to the NOS isoforms control sites can be developed. Initial agents that were designed and tested, as described below in the Examples, were synthetic variants of the autoinhibitory elements of constitutive NOS isoforms, neighboring structural elements, and complements (including antibodies) to these elements. The agents include peptides which have been identified as potent inhibitors, and agents having the same or substantially the same characteristic properties of these inhibitors, including charge arrays such as the polybasic sequences found in the control elements and their complements.

Developmental strategies for agent design take several forms. Starting with the existing inhibitory peptides, homologous or similar peptides are sought which increase the potency of inhibition, or which improve isoform specificity. These homologous or similar sequences can be identified either by mass screening of related sequences or by sequential variations to rationally design a superior variant. Furthermore, peptidomimetics can be devised utilizing the established importance of the polybasic array in inhibitor potency. For example, a peptidomimetic can be designed by substituting the peptidic backbone of the molecule with an alternative oganic or inorganic backbone, whereby the basic moieties are arranged and/or presented in the same three-dimensional configuration. Steric hindrance can be introduced to improve specificity and libraries of charge complemented (primarily negative) molecules can be screened to find agents that bind to the control site elements themselves.

Agents of the Invention

Agents which modulate NOS enzyme activity include agents having an array of positively charged residues or molecules, such as the array of positively charged amino acids in ENOS-homologous peptides. This agent can modulate an NOS enzyme activity by effecting electron transport between NADPH and the active site of an NOS enzyme. Other agents have at least one functional group, and may have two or more functional groups, which bind to the INOS-specific peptide; or have at least one functional group, and may have two or more functional groups, which bind to the recognition site of the inhibitory peptide in a constitutive NOS enzyme, or a homologous region in inducible NOS, and thereby modulate INOS activity. The functional group(s) of the agent can be, for example, amine groups, which bind to a carboxy group within the INOS-specific peptide. For example, as described in Example 2 below, certain peptides of the invention have been shown to inhibit the activity of INOS. These peptides are useful as agents which modulate INOS activity.

In addition, agents that bind to neighboring structural elements can also serve as either activators or inhibitors by interfering with CAM binding, with the active or inactive conformation of the intrinsic autoinihibitory element, or by sterically mimicking the inhibitory effect of the autoinhibitory element. For example, the negatively charged flanking loop regions form the NOS FMN binding domains are neighboring structural elements that can serve as activators or inhibitors of NOS isoforms. Representative agents include antibodies for the synthetic peptide analogs of the NOS control elements and neighboring structural elements. For example, antibodies which are raised to the INOS-specific polypeptide (SEQ. ID. NO. 3) and/or related regions, can be used as agents which modulate INOS activity without modulating the activity of a constitutive NOS enzyme, because they specifically bind to INOS, but not to a constitutive NOS enzyme. Antibodies raised to polypeptides comprising one or both of the two negatively charged loops on the surface of the FMN binding molecule present in all known NOS isoforms, also modulate INOS activity without modulating the activity of a constitutive NOS enzyme. The two negatively charged loops are exposed in INOS, but are not in the constitutive NOS enzymes, because the sites appear to serve as the binding site for the regulatory peptides in ENOS and NNOS, and are therefore covered by the positively charged regulatory peptide, or by the regulatory peptide and calmodulin. Antibodies raised to a NOS regulatory peptide (such as SEQ. ID. NO. 1 or NO. 2), or a polypeptide comprising the NOS regulatory peptide and/or related regions, can be used as agents which modulate the activity of constitutive NOS enzymes without modulating the activity of INOS, as they specifically bind to constitutive NOS enzymes, but not to INOS.

In preferred embodiments, the agent modulates the activity of INOS, without modulating the activity of a constitutive NOS enzyme (ENOS and/or NNOS); alternatively, the agent modulates the activity of constitutive NOS enzymes, without modulating the activity of INOS. In an even more preferred embodiment, the agent modulates the activity of one constitutive NOS enzyme (ENOS or NNOS), and does not modulate the activity of the other constitutive NOS enzyme. The agents of the invention include peptides, as well as antibodies, and peptidomimetics which have the same or similar activity as the peptides, as described below.

Peptides

A series of peptides has been constructed and tested for the ability to modulate the activity of (e.g., inhibit and/or activate) the various NOS isoforms. Thus, these substantially isolated peptides relating to the regulatory peptides of NOS proteins, as well as other related peptides can serve as agents that modulate NOS activity. A "substantially isolated" peptide, as described herein, refers to a peptide that has been derived or removed from the environment in which it naturally occurs. Examples include a peptide fragment derived or removed from the native protein, comprising or consisting essentially of the cited sequences. For example, a substantially isolated peptide would include the cited sequence, the sequence flanked by one or more amino acids which are the same as or different from the amino acid sequence of the native protein. A peptide that inhibits a NOS enzyme is referred to herein as a "nitric oxide synthase inhibitor peptide;" a peptide that activates a NOS enzyme is referred to herein as a "nitric oxide synthase activator peptide".

The peptides of the invention include the ENOS regulatory peptide, MSGPYNSSPRPEQHKSYKIRFNSVSCSD-PLVSSWRRKRKESSNTD (SEQ ID NO. 1); the NNOS regulatory peptide, MRHPNSVQEERKSYKVRFNSVS-SYSDSRKSSGDGPDLLRDNFE (SEQ ID NO. 2); the INOS specific peptide (SEQUENCE) (SEQ ID NO. 3); the regulatory region between about amino acids 590–650 of ENOS; the regulatory region between about amino acids 820–880 of NNOS; and the negatively charged loops of INOS (amino acids 568–581 (SEQ ID NO. 4) and 633–647 (SEQ ID NO. 5)); ENOS (amino acids 557–570 (SEQ ID NO. 6) and 666–680 (SEQ ID NO. 7); and NNOS (amino acids 790–803 (SEQ ID NO. 8) and 897–911 (SEQ ID NO. 9). The peptides of the invention additionally include derivatives of the ENOS regulatory peptide, NNOS regulatory peptide, INOS specific peptide, regulatory regions of ENOS and NNOS, and negatively charged loops of INOS, ENOS and NNOS. A "derivative" of a peptide, as described herein, is a peptide which has one or more amino acids deleted or inserted, or has one or more conservative substitutions. A "conservative substitution", as used herein, is the replacement of a first amino acid with a second amino acid that is similar to the first amino acid in charge, polarity, reactivity, and/or structure. Conservative substitutions include amino acid substitutions within the following groupings: S, T, G, A, and P; L, M, I, and V; E, D, Q, and N; R, H, and K; and F, Y, and W. Fragments of these peptides can also serve as agents that modulate NOS activity. A fragment of a peptide that inhibits NOS activity is referred to herein as an "inhibitory fragment;" a fragment of a peptide that activates NOS activity is referred to herein as an "activating fragment."

The invention further encompasses peptides that are closely related to the ENOS control region, NNOS control region, INOS specific peptide, regulatory regions of ENOS and NNOS, and negatively charged loops of INOS, ENOS and NNOS, as shown by the degree of homology, and, in the case of some peptides based on autoinhibitory elements, by the presence of a core region containing an array of positively charged amino acids. These closely related peptides are referred to herein as "homologous peptides". The core region of a peptide homologous to the ENOS regulatory peptide contains an array of positively charged amino acids. The array has at least two, and preferably at least five, positively charged amino acids. At least two of the positively charged amino acids must be contiguous. The positively charged amino acids can be naturally-occurring or synthetic. In a preferred embodiment, each positively charged amino acid is lysine, arginine, histidine, or ornithine. In a more preferred embodiment, the core region is RRKRK (SEQ ID NO. 10); in another preferred embodiment, the core region is KKRKR (SEQ ID NO. 11). The homologous eptides of the invention are at least 60% homologous, or about 67% homologous, or about 80% homologous, or about 90% homologous to either a section of the ENOS regulatory peptide (SEQ ID NO. 1), the NNOS regulatory peptide (SEQ ID NO. 2), or the INOS specific peptide (SEQ ID NO. 3). The percent of homology indicates the amount of identity (or similarity) between the amino acid sequences of two peptides. The percent similarity takes into consideration close or conservative substitutions in amino acids. In a particularly preferred embodiment, the sequence of the homologous peptide is substantially the same as the identified sequence.

In one embodiment, a homologous peptide of the invention is a substantially isolated peptide having an array of positively charged amino acids, and an amino acid sequence of at least about 60% homology, or about 67% homology, or about 80% homology, or about 90% homology, or is substantially the same as, the amino acid sequence of the ENOS control region (SEQ ID NO. 1). In a preferred embodiment, the substantially isolated peptide binds to a site spatially adjacent to the calmodulin binding site of ENOS. Particular peptides include WRRKRK (SEQ ID NO. 12); SSWR-RKRKESS (SEQ ID NO. 13); SSPRPEQHKSYKIRFNS-VSCSDPLVSSWRRKRKESS (SEQ ID NO. 14); and QHKSYKIRFNSVSCSDPLVSSWRRKRKE (SEQ ID NO. 15).

In another embodiment, a homologous peptide of the invention is a substantially isolated peptide having an amino acid sequence of at least about 60% homology, or about 67% homology, or about 80% homology, or about 90% homology to, or substantially the same as, the amino acid sequence of the NNOS control region (SEQ ID NO. 2). In a preferred embodiment, the substantially isolated peptide binds to a site that is spatially adjacent to the calmodulin binding site of NNOS. Particular peptides include QEERKSYKVRF (SEQ ID NO. 16), RPEQHKSYKIRF (SEQ ID NO. 17), SDSRKSSGDGPDLR (SEQ ID NO. 18), and QEERKSYKVRFNSVSSYSDSQKSSGDGPDL (SEQ ID NO. 19).

In further embodiments, other homologous peptides include a substantially isolated peptide having an amino acid sequence of at least about 60% homology, or about 67% homology, or about 80% homology, or about 90% homology to, or substantially the same as, the amino acid sequence of the INOS specific peptide (SEQ ID NO. 3); and a substantially isolated peptide having an amino acid sequence of at least about 60% homology, or about 67% homology, or about 80% homology, or about 90% homology to the negatively charged loops of the NOS enzymes (SEQ ID NO. 4 and 5 (INOS); 6 and 7 (ENOS), and 8 and 9 (NNOS)).

The peptides of the invention can be prepared using conventional synthetic methods. Alternatively, they can be prepared using conventional methods of molecular genetics (see Sambrook, J. et al., Molecular Cloning: A Laboratory Manual, Cold Spring Harbor Press, Cold Spring Harbor, N.Y. (1989)). The peptides of the invention can also be prepared as fusion peptides with other peptide or proteins, or with other macromolecules, such as polysaccharides.

Antibodies to the Peptides

The peptides of the invention can be used to raise antibodies. Antibodies which are raised to the peptides can be either monoclonal or polyclonal. The term "antibody", as used herein, encompasses both polyclonal and monoclonal antibodies, as well as mixtures of more than one antibody (e.g., a cocktail of different types of monoclonal antibodies) reactive with a peptide of the invention. The term antibody is further intended to encompass whole antibodies and/or biologically functional fragments thereof. Biologically functional antibody fragments which can be used are those fragments sufficient for binding of the antibody fragment to the peptide. Once the antibodies are raised, they are assessed for the ability to bind to the peptide. Conventional methods can be used to perform this assessment.

Monoclonal antibodies (mAb) reactive with a peptide of the invention can be produced using somatic cell hybridization techniques (Kohler and Milstein, *Nature* 256: 495–497 (1975)) or other techniques. In a typical hybridization procedure, a crude or purified NOS enzyme or a peptide of the invention as described above, (e.g., INOS-specific polypeptide, ENOS regulatory peptide, NNOS regulatory peptide, a homologous peptide, or a derivative peptide, as described above), can be used as the immunogen. An animal is immunized with the immunogen to obtain antibody-producing spleen cells. The species of animal immunized will vary depending on the specificity of mAb desired. The antibody producing cell is fused with an immortalizing cell (e.g., a myeloma cell) to create a hybridoma capable of secreting antibodies to the peptide of the invention. The unfused residual antibody-producing cells and immortalizing cells are eliminated. Hybridomas producing desired antibodies are selected using conventional techniques and the selected hybridomas are cloned and cultured.

Polyclonal antibodies can be prepared by immunizing an animal in a similar fashion as described above for the production of monoclonal antibodies. The animal is maintained under conditions whereby antibodies reactive with the peptide of the invention are produced. Blood is collected from the animal upon reaching a desired titer of antibodies. The serum containing the polyclonal antibodies (antisera) is separated from the other blood components. The polyclonal antibody-containing serum can optionally be further separated into fractions of particular types of antibodies (e.g., IgG, IgM).

Antibodies raised to either the regulatory peptide of a constitutive NOS enzyme (ENOS or NNOS), or to the INOS-specific polypeptide, can be used to distinguish constitutive NOS enzymes from INOS, and vice versa. NNOS can be distinguished from ENOS and INOS, because NNOS has a long N terminal extension that is lacking in ENOS and INOS; antibodies to the regulatory peptide or to the INOS-specific polypeptide can now be used to distinguish ENOS from INOS. The potential for cross reactivity between NOS isoforms exists for antibodies to all other regions on the NOS surface except the regulatory peptide and the INOS-specific polypeptide. Antibodies can also be used as agents which alter the activity of a NOS protein, as described further below.

Peptidomimetics and Other Agents

Peptidomimetics (molecules which are not polypeptides, but which mimic aspects of their structures to bind to the same site), that are based upon the above-described peptides, can also be generated. For example, polysaccharides can be prepared that have the same functional groups as the peptides of the invention, and which interact with NOS enzymes in the same manner. Peptidomimetics can be designed, for example, by establishing the three dimensional structure of the peptide agent in the environment in which it is bound or will bind to the enzyme. The peptidomimetic comprises at least two components, the binding moiety or moieities and the backbone or supporting structure.

The binding moieities are the chemical atoms or groups which will react or complex (as informing a hydrogen or covalent bond) with the amino acid(s) at the binding site of the enzyme. In general, the binding moieties in a peptidomimetic are the same as the peptide agent. Alternatively, the binding moieties can be an atom or chemical group which will react with the enzyme in the same or similar manner. Examples of binding moieties suitable for use in designing a peptidomimetic for a basic amino acid in a peptide are nitrogen containing groups, such as amines, ammoniums, guanidines and amides or phosphoniums. Examples of binding moieties suitable for use in designing a peptidomimetic for an acidic amino acid can be, for example, carboxyl, lower alkyl carboxylic acid ester, sulfonic acid, a lower alkyl sulfonic acid ester or a phosphorous acid or ester thereof.

The supporting structure is the chemical entity that, when bound to the binding moiety or moieties, that provides the three dimensional configuration of the peptidomimetic. The supporting structure can be organic or inorganic. Examples of organic supporting structures include polysaccharides, polymers or oligomers of organic synthetic polymers (such as, polyvinyl alcohol or polylactide). It is preferred that the supporting structure possess substantially the same size and dimensions as the peptide backbone or supporting structure. This can be determined by calculating or measuring the size of the atoms and bonds of the peptide and peptidomimetic. In one embodiment, the nitrogen of the peptide bond can be substituted with oxygen or sulfur, thereby forming a polyester backbone. In another embodiment, the carbonyl can be substituted with a sulfonyl group or sulfinyl group, thereby forming a polyamide. Reverse amides of the peptide can be made (e.g., substituting one or more —CONH— groups for a —NHCO— group). In yet another embodiment, the peptide backbone can be substituted with a polysilane backbone.

These compounds can be manufactured by known methods.

For example, a polyester corresponding to the peptide RRKRK can be prepared by the substituting a hydroxyl group for each corresponding amine group on the R and K amino acids, thereby preparing a hydroxyacid and sequentially esterifying the hydroxyacids, optionally blocking the basic side chains and acids to minimize side reactions. Determining an appropriate chemical synthesis route can generally be readily identified upon determining the chemical structure using no more than routine skill.

In addition, large libraries of agents, such as those libraries that can be constructed using well-known methods of combinatorial chemistry, can be assayed for additional agents. Such agents can be isolated through methods described herein are considered to be equivalent to the described agents, in that they interact with the same site on the NOS protein, fulfill the same function (e.g., alter the activity of (inhibit or activate) a specific isoform), and therefore, can be used to treat one or more diseases in which the inhibition or activation of a specific NOS isoform is beneficial. This disclosure therefore encompasses such agents as can be prepared by one skilled in the art through the use of the discoveries and methods described herein.

Probes of the Invention

Isolated nucleic acid probes, which optionally may encode the peptides of the invention, as described above, can also be prepared. Nucleic acid probes, particularly those encoding or corresponding to the regulatory peptide of the constitutive NOS enzymes, ENOS and NNOS (SEQ. ID. NO. 1 and NO. 2) or to the INOS-specific polypeptide (SEQ.

ID. NO. 3), can be used as markers for identifying and mapping NOS enzyme isoforms in humans and other organisms, as well as for probes for specific NOS enzyme genes and mRNA, and for identification of other enzymes with undiscovered but related regulatory sites. The nucleic acid probes can comprise RNA, cDNA, or genomic DNA. The nucleic acid probes substantially correspond to the native nucleic acids encoding or substantially corresponding to the regulatory peptide of the constitutive NOS enzymes, ENOS and NNOS (SEQ. ID. NO. 1 and NO. 2), the INOS-specific polypeptide (SEQ. ID. NO. 3), or derivative or homologous peptides. To identify NOS enzyme isoforms or related enzymes, a DNA or RNA sample (a test sample) is obtained from the organism of interest; the test sample is contacted with a nucleic acid probe, under hybridization conditions which allow hybridization of the nucleic acid probe to homologous DNA or RNA in the test sample. Stringency hybridization conditions can be adjusted to eliminate hybridization to extraneous sequences (see Sambrook, J. et al., Molecular Cloning: A Laboratory Manual, Cold Spring Harbor Press, Cold Spring Harbor, N.Y. (1989)). The presence (or absence) of hybridization is then detected, using conventional methods. The homologous DNA or RNA, if present, can be isolated for further study.

Nucleic Acid Molecules of the Invention

Isolated nucleic acid molecules which encode the peptides of the invention, as described above, as well as nucleic acid molecules complementary to the nucleic acid molecules, can also be prepared, using standard techniques (see Sambrook, J. et al., Molecular Cloning: A Laboratory Manual, Cold Spring Harbor Press, Cold Spring Harbor, N.Y. (1989)). Such isolated nucleic acid molecules can be used to prepare peptides of the invention. In addition, isolated nucleic acid molecules which encode the antibodies of the invention, as described above, as well as complementary nucleic acid molecules, can also be prepared and used to generate antibodies of the invention.

Methods of Treatment

The agents that modulate NOS enzyme activity, as described above, can be used to modulate the activity of a nitric oxide synthase enzyme in vivo. In a preferred embodiment, the agent is used to modulate the activity of a nitric oxide synthase in a mammal, such as a human, in order to treat a disease or condition associated with NO production in the mammal. An agent which modulates the activity of INOS, or of a constitutive NOS enzyme (NNOS or ENOS), is administered to the mammal. The agent can be administered subcutaneously, intravenously, intramuscularly, intraperitoneally, topically, orally, rectally, nasally, buccally, vaginally, intraurethrally, by inhalation spray, or via an implanted reservoir. Where the agent is a peptide, the agent can also be administered via a gene transfer vector containing a nucleic acid encoding the peptide. Administration of the gene transfer vector leads to expression of a nucleic acid sequence, resulting in production of the peptide and modulation of the specific NOS isoform. A gene transfer vector containing a nucleic acid encoding the peptide can also contain tissue-specific promoters, as well as other elements (e.g., enhancer elements, splicing signals, termination and polyadenylation signals, viral replicons, bacterial plasmid sequences, or other vector nucleic acid sequences). Delivery of the vector can be targeted to particular regions or cell types (e.g., by the use of decorated liposomes, or by introducing the vector in a specific region). For example, transformation of cells with a peptide that inhibits INOS activity would be effective protection against NO-related islet cell destruction in those at risk for early onset diabetes. In another example, transformation of endothelial cells with a peptide that activates ENOS can be used for long-term treatment of hypertension.

If the agent is an antibody, gene transfer methods can also be used to administer a nucleic acid encoding the antibody or a fragment of the antibody. Administration of the vector leads to expression of the nucleic acid sequence, resulting in production of the antibody, and, ultimately, modulation of the specific NOS isoform.

The agent can be administered in dosage formulations containing conventional, non-toxic, physiologically-acceptable carriers, adjuvants, and/or vehicles. The form in which the agents are administered will depend at least in part on the route by which they are administered.

The agent is administered in an effective amount, which is that amount necessary to modulate the NOS enzyme. In treatment of a disease or condition, the agent is administered in a therapeutically effective amount. A therapeutically effective amount is that amount necessary to reduce or eliminate symptoms associated with the disease or condition. The effective amount, or the therapeutically effective amount, will be determined on an individual basis, and will be based in part, on consideration of the agent, the individual's size and gender, the severity of the symptoms to be treated, the result sought, the disease, etc. Thus, the therapeutically effective amount can be determined by one of ordinary skill in the art, employing such factors and using no more than routine experimentation.

The therapeutically effective amount can be administered in a single dose, or a series of doses separated by appropriate intervals, such as hours, days, or weeks. The term "single dose," as used herein, can be a solitary dose, and can also be a sustained release dose, such as by a controlled-release dosage formulation or a continuous infusion. Other drugs can also be administered in conjunction with the agent; e.g., a vasopressor administered in conjunction with an INOS inhibitor for septic shock treatment. More than one agent which modulates the activity of a NOS enzyme can be administered at the same time.

In one embodiment of the invention, an agent which modulates, and particularly, which increases the activity of ENOS, is administered, in order to treat a condition modulated by production of nitric oxide by endothelial nitric oxide synthase, such as hypertension, atherosclerosis, or acute asthma. In a preferred embodiment, the agent does not modulate the activity of NNOS or INOS. An agent which increases ENOS activity will allow NO to be produced directly adjacent to the site of action. Since such an activator would not have to dissociate to produce NO, it would be stable and would not need to be "used up" to be effective. This is due to the mode of action of the agent; it turns on a catalyst, and each molecule of agent can cause the production of many molecules of NO gradually over a long time course. In contrast, NO donors such as nitroglycerin are limited by the number of NO groups they contain (usually 1–3) and must be replaced as they are used up to produce NO.

In the case of constitutive NOS enzymes (NNOS or ENOS), an agent which activates either ENOS and/or NNOS in the corpus cavernosa can be used as a means for treating male erectile dysfunction. In one embodiment, the agent is administered intraurethrally to limit systemic side effects.

In another embodiment, an agent which specifically inhibits NNOS can be used to prevent brain damage in conditions involving cerebral ischemia/reperfusion injury, such as head trauma.

In another embodiment, an agent which modulates, and particularly, which decreases the activity of INOS is administered in order to treat a condition modulated by production of nitric oxide by INOS, such as septic shock, toxic shock, autoimmune disease such as rheumatoid arthritis, inflammatory conditions such as inflammatory bowel disease, multiple sclerosis, or diabetes. In a preferred embodiment, the agent which modulates INOS activity does not modulate the activity of NNOS or ENOS. Furthermore, INOS is important in dementia associated with Acquired Immune Deficiency Syndrome (AIDS), and may be involved in the destruction of the immune system and general physical deterioration produced by the AIDS virus (Baldeway, T., et al., *AIDS* 10451–452 (1996); Brenner, T., et al., *Brain Res.* 641:51–56 (1994); Lipson, S. A., *Devel. Neurosci.* 94:145–151 (1996); Buck, M. et al., *EMBO J.* 151753–1763 (1996); Cross, et al., *J. Clin. Invest.* 93:2684–2650 (1994); Boulleme, A. I. et al., *J. Neuroimmunol.* 60:117–124 (1995); Mayer, M., *Nervenarzt* 65:819–827 (1994)). Therefore, an agent which modulates the activity of INOS can be administered to combat dementia, immune system destruction, and/or physical deterioration in individuals infected with the AIDS virus. Further, an agent which activates INOS can be used to treat diseases relating to dysplasia, cancer, or infectious disease. Activation of INOS can produce cytotoxic levels of NO which would aid in the elimination of dysplastic or cancerous tissue, or aid in the control of infectious agents such as viruses, microbes, or other parasites.

The following examples are further illustrative of the present invention.

EXAMPLE 1

Identification of the Nitric Oxide Synthase Regulatory Region

A. Structure of Nitric Oxide Synthase Enzymes

All nitric oxide synthase (NOS) enzymes are modular in nature: they consist of a series of connected regions, each of which is closely related to a small simple protein. The C-terminal region of NOS is homologous to two flavoproteins, ferredoxin NADP reductase (a flavin adenine dinucleotide (FAD)-linked enzyme), and flavodoxin (a small flavin mononucleotide (FMN) binding protein). The corresponding regions in NOS function together to bring electrons into the enzyme for production of NO from arginine and oxygen. Binding of calmodulin by NNOS and ENOS turns on electron transfer from the flavin binding region to the active site, which contains a heme cofactor. The calmodulin binding site in all three types of NOS is located close to the N-terminal edge of the flavodoxin module.

Almost immediately (within ten residues) after the calmodulin binding site in each NOS there is a region with the sequence TETGKSEALA (SEQ ID NO. 20) or a close homologue. This sequence is recognized as the homologue of closely related flavodoxin sequences such as TDTGKTEALA (SEQ ID NO. 21), which are involved in binding the flavin cofactor. These sequences form a dense hydrogen bond network with the phosphate group of flavin mononucleotide (FMN).

B. Alignment of Sequences

The sequences of about twenty flavodoxins were aligned with the corresponding regions of all available NOS sequences and with the sequences of NADPH cytochrome P450 reductase (NCPR). NCPR is a related flavoprotein which, like NOS, has both the FMN and FAD binding domains, but is unregulated and lacks a calmodulin binding site. All known NOS isoforms contain two negatively charged loops on the surface of the FMN binding molecule. INOS itself contains a surface polypeptide not found in either ENOS or NNOS. This surface polypeptide, having the sequence of amino acids 600–615 of INOS (SEQ ID NO. 3), is referred to herein as the "INOS-specific polypeptide".

Computer alignment of the flavoprotein sequences failed to align or identify the TETGKSEALA (SEQ ID NO. 20) regions because of a large insertion in the constitutive NOS enzymes (NNOS and ENOS), and because available programs do not make use of three dimensional structural information. The TETGKSEALA (SEQ ID NO. 20) region and the previously recognized conserved sequences which make up the FMN binding site were aligned by hand. The FIGURE shows an alignment of a selected set of NOS, NCPR and bacterial flavodoxin sequences. NCPR HUMAN, human NADPH P450 reductase (SEQ ID NO. 29); NOSE BOVIN, bovine ENOS (SEQ ID NO. 30); NOSE RAT, rat NNOS (SEQ ID NO. 31); NOSM MOUSE, mouse INOS (SEQ ID NO. 32); FLAV ECOLI, *Escherichia coli* flavodoxin (SEQ ID NO. 33); and FLAV DESVH, *Desulfovibrio vulgaris* flavodoxin (SEQ ID NO. 34). Critical regions, which were identified based on the three dimensional structures of flavodoxins that have been solved by X-ray crystallography were forced to align.

C. Identification of Regulatory Region

The pattern of the insertions, identified by the alignment, revealed the control mechanism of nitric oxide synthase. Compared to flavodoxins, which lack a calmodulin binding side, NCPR has no insertions of more than five residues after the TETGKSEALA (SEQ ID NO. 20) region in the FMN binding domain. Immune (macrophage) NOS (INOS or MNOS), which binds calmodulin but does not respond to calcium, also lacks an insertion in the corresponding region. In contrast, the constitutive NOS isoforms (ENOS and NNOS), which bind calmodulin and are under calcium control, have extensive (40–45 residues) insertions within the FMN binding domain. This is the critical difference between the constitutive and inducible isoforms of NOS.

The insertions are about 100 residues downstream (towards the C terminus) from the calmodulin binding site. On the published three-dimensional structure of flavodoxin (Wapenpaugh, K., et al., *PNAS* 70:3852–3860 (1973)), this insertion lies on an external loop at one edge of the beta sheet which forms the core of the protein. The insert is spatially adjacent to the calmodulin binding site.

Since the insert is about 30% as large as a flavodoxin molecule, and calmodulin is comparable in size to flavodoxin, it is clear that steric effects are important. Calmodulin binding to INOS is unusually tight, partly because of the absence of interference from the insert. In ENOS and NNOS, since the insert and calmodulin cannot occupy the same space, calmodulin binding forces the insert out of the way. It is this interaction between calmodulin and the insert which turns the enzyme on. Thus, ligands which interact with the insert and the adjacent region of the FMN domain will therefore tend to force the switching mechanism into the off state or the on state. In other calmodulin regulated systems, such ligands may produce a weakly active state in the absence of calmodulin; this weakly active state is resistant to further activation. The negatively charged loops on the surface of the FMN binding domain appear to serve as the binding site for the regulatory peptides in ENOS and NNOS. The regulatory polypeptide in INOS is the short loop which is split and greatly extended by the introduction of the regulatory peptides in ENOS and NNOS.

D. Structural Models

The availability of solved X-ray structures for flavodoxins allows us to position the insertion in three dimensions relative to the calmodulin binding site. Homology-based molecular models were constructed for the FMN binding domains of constitutive NOS, INOS and p450 reductase. These models were constructed using the Insight and Homology programs (Biosym, Inc.), and could be relaxed to a sterically and energetically reasonable state using Discover software (Biosym, Inc.).

The backbones of the INOS and p450 reductase modules can be almost superimposed on the backbone of desulfovibrio flavodoxin, which appears to be the closest solved structural homolog of the FMN binding modules of the NOS isoforms. The structure, a Rossman fold motif, is a five-stranded, parallel β sheet, with the FMN binding site along one edge. Two aromatic residues, W and Y in INOS, are in contact with the FMN ring system; the latter serves as a shielding residue.

Most of the corresponding backbone structure of ENOS can be superimposed on the structures of INOS and p450 reductase modules, but the insertion projects from the edge of the sheet opposite the FMN binding site. The backbone of NNOS is similar to ENOS. Structurally, the insertion corresponds to the replacement of a tight 5–10 residue α>β loop with an approximately 50 residue structure which is about ⅓ the size of the entire FMN binding module. The conformation for the insertion is currently unknown.

The calmodulin binding site is directly adjacent to the N terminal edge of the FMN binding domain. When calmodulin is bound, the site must be in a helical conformation, and can then be expected to extend almost directly away from the FMN binding domain because of steric constraints. Calmodulins (m.w. approximately 20 kD) are considerably larger than the entire FMN binding module. Although the insertion is midway through the sequence of the FMN binding module, it is immediately apparent that in three dimensions it is directly adjacent to the CAM binding site. Clearly, CAM binding is likely to be sterically hindered by the insertion, and probably demands that the insertion undergo conformational reorganization. It is therefore likely that the insertion has more than one physiologically relevant conformation.

The proximity of the CAM binding site to the insertion, their probable steric interactions, and the correlation between calcium/calmodulin control and the presence of the insertion strongly suggest that the insertion functions as a control element. An attractive potential role is that of an inhibitory polypeptide displaced by CAM binding. It would differ from the inhibitory polypeptides in other systems, in that it is not a CAM analog, but would be displaced from a neighboring site because of binding domain overlap.

EXAMPLE 2

Synthetic Polypeptide Effects

In order to evaluate the functional significance of the putative inhibitory polypeptide, a series of synthetic polypeptides were designed which incorporated structural features of loop regions in the FMN domain. Polypeptides corresponding to promising recognition sites such as the RRKRK motif were synthesized in lengths ranging from six to thirty five residues, as shown in Table 1, below. Polypeptides corresponding to both the ENOS and NNOS insertions were selected for evaluation. In addition to constructs based on the major insertions, polypeptides corresponding to the neighboring a>: loops in all three isoforms were synthesized, because of the possibility that these loops form a significant part of the binding site for the insertion in NOS. This possibility was suggested both by their proximity to the insertion and by their negative charge.

TABLE 1

Synthetic Peptides

| Peptide | Der.[1] | Sequence | SEQ ID NO. |
|---|---|---|---|
| B058-01 | h ENOS | AVDTRLEELGGERT | 21 |
| B058-02 | NNOS | AVDTLLEELGGERT | 22 |
| B058-03 | m INOS | DIDQKLSHLGASQT | 23 |
| B058-04 | b ENOS | DDVVSLEHET | 24 |
| B058-05 | r NNOS | DIVHLEHES | 25 |
| B058-06 | m INOS | KASTLEEEQ | 26 |
| B058-07 | b ENOS | WRRKRK | 12 |
| B058-08 | b ENOS | SSWRRKRKESS | 13 |
| B058-09 | h NNOS | QEERKSYKVRF | 16 |
| B058-10 | h NNOS | RPEQHKSYKIRF | 17 |
| B058-11 | r NNOS | SDSRKSSGDGPDLR | 18 |
| JX2 | b ENOS | SSPRPEQHKSYKIRFNSVSCSDPLVSSWRRKRKESS | 14 |
| JX3 | b ENOS | QHKSYKIRFNSVSCSDPLVSSWRRKRKE | 15 |
| JX4 | h NNOS | QEERKSYKVRFNSVSSYSDSQKSSGDGPDL | 19 |
| PEP1 | | RPEQHKSYKIRF | 27 |
| PEP2 | | QEERKSYKVRFNSVSSYSDSRKSSGDGPDL | 28 |

[1]Derivation: h = human; m = mouse; b = bovine and r = rat.

JX series polypeptides are approximately 30-mers derived from ENOS and NNOS inhibitory polypeptides. BO58 series are shorter (6-mers to 15-mers) peptides derived from flanking loops or from shorter segments of inhibitory polypeptides. CAM binding data represents counts from radiolabeled CAM trapped on a membrane by NNOS adhesion. INOS activity was assayed by measuring oxidation of ferrous myoglobin by product NO. Mg/ml concentrations of larger JX series polypeptides were three times higher than others to keep molar concentrations comparable in experiments. The results of experiments to determine the effects of the synthetic polypeptides on NOS activity are shown in Table 2, below.

TABLE 2

CAM Binding and INOS Inhibition Data

| Peptide | NNOS CAM Binding | INOS Activity 0.1 mg/ml | INOS activity 0.3 mg/ml | INOS Activity 1.0 mg/ml |
|---|---|---|---|---|
| None | 774 ± 40 | 14.9 ± .56 | 12.3 ± .19 | 13.0 ± .23 |
| B058-01 | 986 ± 58 | 15.0 ± .73 | | |
| B058-02 | 953 ± 80 | 15.1 ± .03 | | |
| B058-03 | 863 ± 19 | 14.4 ± .27 | | |
| B058-04 | 903 ± 57 | 15.8 ± .73 | 14.9 ± .56 | |
| B058-05 | 952 ± 52 | 14.6 ± .03 | | |
| B058-06 | 951 ± 100 | 15.3 ± .32 | | |
| B058-07 | 1749 ± 40 | 13.6 ± .31 | | |
| B058-08 | 152 ± 26 | 14.5 ± .70 | | |
| B058-09 | 686 ± 43 | 14.7 ± .28 | | |
| B058-10 | 1339 ± 49 | 14.6 ± .02 | | |
| B058-11 | 908 ± 56 | 14.7 ± .94 | | |
| JX2 | 1356 ± 46 | 13.1 ± .11 | 7.7 ± .11 | 3.2 ± .11 |
| JX3 | 674 ± 100 | 12.9 ± .32 | 7.9 ± .11 | 2.9 ± .32 |
| JX4 | 659 ± 41 | 14.1 ± .57 | 10.4 ± .57 | 8.4 ± .57 |

A second experiment confirmed these results. NOS activity measurements were performed using recombinant rat NNOS (purified from overexpressing HEK293 cells), recombinant bovine ENOS (purified from overexpressing E. coli) or native INOS (from immunostimulant-activated rat aortic smooth muscle cells). Activity was determined with 1–20 pmole of NOS using a kinetic 96-well microtiter plate assay based on the kinetics of NADPH consumption (NNOS and ENOS) or Fe 2+-myoglobin oxidation. Radioligand binding was performed after incubation of 1–2 pmole of NOS for 15 minutes at 23° C. with either Bolton-Hunter labelled [125I]-calmodulin (1 nM) or [3H]-N-nitro-L-arginine (200 pM) and the indicated peptides. Results are shown in Table 3. Values are means±SEM of triplicate determinations.

TABLE 3

Effect of Peptides on NOS Activity and Ligand Binding

| Peptide | μg/ml (μM) | NOS Activity (% of control) | | | Ligand binding to NOS | |
|---|---|---|---|---|---|---|
| | | NNOS | ENOS | INOS | [$^3$H]-NHA | [$^{125}$I]-CAM |
| B058-07 | 100 (107.0) | 11.0 ± 3.3 | 24.0 ± 2.8 | 91.1 ± 5.7 | 91.7 ± 5.1 | 6.7 ± 3.6 |
| B058-08 | 100 (71.2) | 19.1 ± 0.9 | 27.7 ± 2.0 | 92.1 ± 1.3 | 120.7 ± 12.7 | 0.0 ± 0.5 |
| B058-09 | 100 (68.1) | 102.0 ± 2.1 | 93.6 ± 2.3 | 101.1 ± 3.7 | 118.9 ± 4.1 | 82.7 ± 1.1 |
| B058-10 | 100 (63.0) | 54.5 ± 1.8 | 80.5 ± 2.0 | 99.7 ± 5.7 | 115.0 ± 8.6 | 24.7 ± 2.2 |
| B058-11 | 100 (72.0) | 98.4 ± 1.9 | 102.6 ± 4.1 | 99.7 ± 2.8 | 119.2 ± 3.4 | 89.2 ± 6.2 |
| JX2 | 300 (76.0) | 30.4 ± 1.7 | 57.2 ± 7.5 | 62.2 ± 2.8 | 116.3 ± 1.9 | 0.0 ± 7.4 |
| JX3 | 300 (87.7) | 28.2 ± 0.9 | 40.2 ± 4.0 | 64.3 ± 3.2 | 122.4 ± 1.0 | 0.0 ± 4.8 |
| JX4 | 300 (84.8) | 103.0 ± 1.3 | 80.2 ± 3.8 | 84.1 ± 3.5 | 95.7 ± 4.7 | 82.7 ± 1.1 |

Several of the polypeptides based on ENOS insertions proved capable of inhibiting INOS activity. A 50% inhibition of INOS was observed within minutes after adding the polypeptides. Since the "off" constant of CAM is many orders of magnitude longer than this time frame, the result suggests that inhibition can be obtained without CAM displacement. If inhibition were dependent on simple competition between CAM and the inhibitor, it would be necessary to wait hours or days for CAM to fall off and be replaced by inhibitory; therefore, a ternary complex must form at least transiently. While it is not possible currently to completely eliminate the possibility that CAM is rapidly displaced from the ternary complex, the fact that, in the absence of peptide boiling, does not completely displace CAM from INOS, suggests that the ternary complex is the inhibited species.

The most effective inhibitory polypeptides contain the motif RRKRK from the ENOS insertion. Partial inhibition of INOS could also be obtained with NNOS-based polypeptides.

EXAMPLE 3
Effects on Calmodulin Binding

In addition to the inhibition of enzyme activity, it is possible to modulate CAM binding to NOS with synthetic homologs of the control site elements. The relationship between enzyme inhibition and CAM binding in the presence of control site elements can be complex. In other systems, antibodies to inhibitory elements sometimes induce partial CAM independent activation, while preventing CAM dependent activation. It is important to remember that CAM binding is only a means to displace the inhibitor.

The results of the experiments not only confirmed the function of the major FMN module insertion as the inhibitory polypeptide, but suggested a few details of the switching mechanism. While a number of the polypeptides could modulate CAM binding, the series containing the RRKRK (SEQ ID NO:10) motive was the most instructive. The peptide with three residues following this motif (RRKRKEES, amino acids 4–11 of SEQ ID NO: 13) was a potent CAM antagonist with ENOS and NNOS. CAM binding was decreased almost to background levels, with effects seen at the 10 uM level.

Polypeptides which terminated at the RRKRK motif, including good inhibitors, were promoters of CAM binding. One polypeptide which had a single amino acid after this motif had no significant effect on CAM binding. Polypeptides based on the flanking loop regions had no significant effect on INOS activity, but tended to weakly promote the binding of CAM to constitutive NOS.

EXAMPLE 4

Mechanism of NOS Control

The results presented here provide powerful evidence that the major insertion in the FMN binding module is the inhibitory polypeptide of constitutive NOS, and that its absence in INOS accounts for the lack of sensitivity of INOS to calcium, and, in part, for its very tight binding of CAM. It appears that INOS has developed from an ancestral constitutive NOS-like protein by loss of the inhibitory peptide. The CAM binding site in INOS and constitutive NOS is apparently related to a similar basic region near the N terminal of P450 reductase, and may have developed from such a region in a common ancestral protein.

The inhibition of INOS by synthetic analogs of the constitutive NOS inhibitory polypeptides is related to the ability of the synthetic polypeptides to modulate CAM binding, but does not have the simple direct relationship expected if the mechanism of peptide inhibitor action was through CAM displacement. The reverse appears to be true: inhibition/activation of NOS at this site is driven by the occupancy of key sites by the inhibitory polypeptide, and CAM binding acts to modify the binding of the intrinsic inhibitory segment to a site or sites nearby on the surface of the enzyme.

It is not necessary to displace CAM in order to inhibit the enzyme at the control site. The data suggest that the binding domain of the inhibitory peptide has several regions. There is at least one recognition site which binds the RRKRK (SEQ ID NO:10)motif, and there is indication of a second such site which recognizes sequences such as EERKSYKVRF (amino acids 2–11 of SEQ ID NO: 16)and EQHKSYKIRF (amino acids 3–12 of SEQ ID NO: 17) which occur in the N terminal half of the ENOS and NNOS insertions; peptides which lack RRKRK (SEQ ID NO:10) but contain these sequences can be inhibitors and/or CAM binding modulators.

Ability to bind to this recognition site does not automatically confer either inhibitory character or the ability to prevent CAM binding. It is apparent that CAM binding is strongly inhibited by peptides with a short extension after the RRKRK (SEQ ID NO:10) motif; a three residue extension produced a peptide which reduced CAM binding to near background levels, while even a single residue produced a small decrease. The ability of the two polypeptides which ended in the RRKRK (SEQ ID NO:10) motif to potentiate CAM binding strongly suggests that a region of overlap between the CAM binding site and the peptide binding site exists, in which the overlap occurs between bound CAM and residues towards the C terminal from RRKRK (SEQ ID NO:10). In the intrinsic peptide other residues may contribute to the overlap, since it is both larger and more conformationally constrained than the synthetic analogs used here as probes.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. An extrinsic activator of endothelial nitric oxide synthase which antagonizes autoinhibition by interacting with an intrinsic peptide region of endothelial nitric oxide synthase, wherein the region consists of amino acids 590–650 of endothelial nitric oxide synthase (SEQ ID NO. 30, aa 78–138).

2. An antibody, or fragment thereof, which binds to an epitope comprising amino acids between about amino acids 590–650 in the regulatory region of endothelial nitric oxide synthase (SEQ ID NO. 30, aa 78–138).

3. The antibody of claim 2, wherein the antibody activates endothelial nitric oxide synthase.

4. A constitutive nitric oxide synthase activator peptide consisting of an amino acid sequence selected from the group consisting of: SEQ ID NO. 4, SEQ ID NO. 5, SEQ ID NO. 6, SEQ ID NO. 7, SEQ ID NO. 8, SEQ ID NO. 9, and activating fragments and derivatives of SEQ ID NO. 4, SEQ ID NO. 5, SEQ ID NO. 6, SEQ ID NO. 7, SEQ ID NO. 8, SEQ ID NO. 9 in which the activator function of the parent compound is conserved.

5. An activator of endothelial nitric oxide synthase which binds to amino acids in a sequence selected from the group consisting of: SEQ ID NO. 21 and SEQ ID NO. 24.

6. A constitutive nitric oxide synthase activator peptide consisting of an amino acid sequence selected from the group consisting of: SEQ ID NO. 4, SEQ ID NO. 5, SEQ ID NO. 6, SEQ ID NO. 7, SEQ ID NO. 8, and SEQ ID NO. 9.

* * * * *

```
                              SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
          (A) LENGTH: 45 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:1:

Met Ser Gly Pro Tyr Asn Ser Ser Pro Arg Pro Glu Gln His Lys Ser
1               5                   10                  15

Tyr Lys Ile Arg Phe Asn Ser Val Ser Cys Ser Asp Pro Leu Val Ser
            20                  25                  30

Ser Trp Arg Arg Lys Arg Lys Glu Ser Ser Asn Thr Asp
        35                  40                  45

(2) INFORMATION FOR SEQ ID NO:2:

(i) SEQUENCE CHARACTERISTICS:
          (A) LENGTH: 43 amino acids
          (B) TYPE: amino acid
          (C) STRANDEDNESS:
```

(D) TOPOLOGY: linear (ii) MOLECULE TYPE: peptide (xi) SEQUENCE DESCRIPTION: SEQ ID NO:2:

Met Arg His Pro Asn Ser Val Gln Glu Glu Arg Lys Ser Tyr Lys Val
1               5                   10                  15

Arg Phe Asn Ser Val Ser Ser Tyr Ser Asp Ser Arg Lys Ser Ser Gly
            20                  25                  30

Asp Gly Pro Asp Leu Leu Arg Asp Asn Phe Glu
            35                  40

(2) INFORMATION FOR SEQ ID NO:3:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Lys Lys Ser Leu Phe Met Leu Arg Glu Leu Asn His Thr Phe Arg Tyr
1               5                   10                  15

(2) INFORMATION FOR SEQ ID NO:4:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Gln Tyr Lys Ala Ser Thr Leu Glu Glu Glu Gln Leu Leu Leu
1               5                   10

(2) INFORMATION FOR SEQ ID NO:5:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

His Asp Ile Asp Gln Lys Leu Ser His Leu Gly Ala Ser Gln Leu
1               5                   10                  15

(2) INFORMATION FOR SEQ ID NO:6:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Glu Tyr Asp Val Val Ser Leu Glu His Glu Ala Leu Val Leu
1               5                   10

```
(2) INFORMATION FOR SEQ ID NO:7:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

Ala Ala Val Asp Thr Arg Leu Glu Glu Leu Gly Gly Glu Arg Leu
1               5                  10                  15

(2) INFORMATION FOR SEQ ID NO:8:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

Glu Tyr Asp Ile Val His Leu Glu His Glu Ala Leu Val Leu
1               5                  10

(2) INFORMATION FOR SEQ ID NO:9:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

His Ala Val Asp Thr Leu Leu Glu Glu Leu Gly Gly Glu Arg Ile
1               5                  10                  15

(2) INFORMATION FOR SEQ ID NO:10:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Arg Arg Lys Arg Lys
1               5

(2) INFORMATION FOR SEQ ID NO:11:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

Lys Lys Arg Lys Arg
1               5
```

(2) INFORMATION FOR SEQ ID NO:12:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

```
Trp Arg Arg Lys Arg Lys
1               5
```

(2) INFORMATION FOR SEQ ID NO:13:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

```
Ser Ser Trp Arg Arg Lys Arg Lys Glu Ser Ser
1               5                   10
```

(2) INFORMATION FOR SEQ ID NO:14:

(i) SEQUENCE CHARACTERISTICS:
        (A) LENGTH: 36 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

```
Ser Ser Pro Arg Pro Glu Gln His Lys Ser Tyr Lys Ile Arg Phe Asn
1               5                   10                  15

Ser Val Ser Cys Ser Asp Pro Leu Val Ser Ser Trp Arg Arg Lys Arg
                20                  25                  30

Lys Glu Ser Ser
            35
```

(2) INFORMATION FOR SEQ ID NO:15:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:15:

```
Gln His Lys Ser Tyr Lys Ile Arg Phe Asn Ser Val Ser Cys Ser Asp
1               5                   10                  15

Pro Leu Val Ser Ser Trp Arg Arg Lys Arg Lys Glu
                20                  25
```

(2) INFORMATION FOR SEQ ID NO:16:

(i) SEQUENCE CHARACTERISTICS:
        (A) LENGTH: 11 amino acids (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:16:

Gln Glu Glu Arg Lys Ser Tyr Lys Val Arg Phe
1               5                   10

(2) INFORMATION FOR SEQ ID NO:17:

(i) SEQUENCE CHARACTERISTICS:
            (A) LENGTH: 12 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:17:

Arg Pro Glu Gln His Lys Ser Tyr Lys Ile Arg Phe
1               5                   10

(2) INFORMATION FOR SEQ ID NO:18:

(i) SEQUENCE CHARACTERISTICS:
            (A) LENGTH: 14 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:18:

Ser Asp Ser Arg Lys Ser Ser Gly Asp Gly Pro Asp Leu Arg
1               5                   10

(2) INFORMATION FOR SEQ ID NO:19:

(i) SEQUENCE CHARACTERISTICS:
            (A) LENGTH: 30 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:19:

Gln Glu Glu Arg Lys Ser Tyr Lys Val Arg Phe Asn Ser Val Ser Ser
1               5                   10                  15

Tyr Ser Asp Ser Gln Lys Ser Ser Gly Asp Gly Pro Asp Leu
            20                  25                  30

(2) INFORMATION FOR SEQ ID NO:20:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:20:

Thr Glu Thr Gly Lys Ser Glu Ala Leu Ala
1               5                   10

(2) INFORMATION FOR SEQ ID NO:21:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:21:

```
Thr Asp Thr Gly Lys Thr Glu Ala Leu Ala
1               5                   10
```

(2) INFORMATION FOR SEQ ID NO:22:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:22:

```
Ala Val Asp Thr Leu Leu Glu Glu Leu Gly Gly Glu Arg Thr
1               5                   10
```

(2) INFORMATION FOR SEQ ID NO:23:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:23:

```
Asp Ile Asp Gln Lys Leu Ser His Leu Gly Ala Ser Gln Thr
1               5                   10
```

(2) INFORMATION FOR SEQ ID NO:24:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:24:

```
Asp Asp Val Val Ser Leu Glu His Glu Thr
1               5                   10
```

(2) INFORMATION FOR SEQ ID NO:25:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:25:

```
Asp Ile Val His Leu Glu His Glu Ser
1               5
```

```
(2) INFORMATION FOR SEQ ID NO:26:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:26:

Lys Ala Ser Thr Leu Glu Glu Glu Gln
1               5

(2) INFORMATION FOR SEQ ID NO:27:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:27:

Arg Pro Glu Gln His Lys Ser Tyr Lys Ile Arg Phe
1               5                   10

(2) INFORMATION FOR SEQ ID NO:28:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:28:

Gln Glu Glu Arg Lys Ser Tyr Lys Val Arg Phe Asn Ser Val Ser Ser
1               5                   10                  15

Tyr Ser Asp Ser Arg Lys Ser Ser Gly Asp Gly Pro Asp Leu
            20                  25                  30

(2) INFORMATION FOR SEQ ID NO:29:

(i) SEQUENCE CHARACTERISTICS:
        (A) LENGTH: 135 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:29:

Glu Ser Ser Phe Val Glu Lys Met Lys Lys Thr Gly Arg Asn Ile Ile
1               5                   10                  15

Val Phe Tyr Gly Ser Gln Thr Gly Thr Ala Glu Glu Phe Ala Asn Arg
                20                  25                  30

Leu Ser Lys Asp Ala His Arg Tyr Gly Met Arg Gly Met Ser Ala Asp
            35                  40                  45

Pro Glu Glu Tyr Asp Leu Ala Asp Leu Ser Ser Leu Pro Glu Ile Asp
        50                  55                  60

Asn Ala Leu Val Val Phe Cys Met Ala Thr Tyr Gly Glu Gly Asp Pro
65                  70                  75                  80
```

```
Thr Asp Asn Ala Gln Asp Phe Tyr Asp Trp Leu Gln Glu Thr Asp Val
                85                  90                  95

Asp Leu Ser Gly Val Lys Phe Ala Val Phe Gly Leu Gly Asn Lys Thr
            100                 105                 110

Tyr Glu His Phe Asn Ala Met Gly Lys Tyr Val Asp Lys Arg Leu Glu
        115                 120                 125

Gln Leu Gly Ala Gln Arg Ile
130                 135
```

(2) INFORMATION FOR SEQ ID NO:30:

(i) SEQUENCE CHARACTERISTICS:
        (A) LENGTH: 168 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:30:

```
Gly Thr Leu Met Ala Lys Arg Val Lys Ala Thr Ile Leu Tyr Ala Ser
1               5                   10                  15

Glu Thr Gly Arg Ala Gln Ser Tyr Ala Gln Gln Leu Gly Arg Leu Phe
            20                  25                  30

Arg Lys Ala Phe Asp Pro Arg Val Leu Cys Met Asp Glu Tyr Asp Val
        35                  40                  45

Val Ser Leu Glu His Glu Thr Leu Val Leu Val Val Thr Ser Thr Phe
    50                  55                  60

Gly Asn Gly Asp Pro Pro Glu Asn Gly Glu Ser Phe Ala Ala Ala Leu
65                  70                  75                  80

Met Glu Met Ser Gly Pro Tyr Asn Ser Ser Pro Arg Pro Glu Gln His
                85                  90                  95

Lys Ser Tyr Lys Ile Arg Phe Asn Ser Val Ser Cys Ser Asp Pro Leu
            100                 105                 110

Val Ser Ser Trp Arg Arg Lys Arg Lys Glu Ser Ser Asn Thr Asp Ser
        115                 120                 125

Ala Gly Ala Gly Thr Leu Arg Phe Leu Cys Val Phe Gly Leu Gly Ser
    130                 135                 140

Arg Ala Tyr Pro His Phe Cys Ala Phe Ala Ala Val Asp Thr Arg Leu
145                 150                 155                 160

Glu Glu Leu Gly Gly Glu Arg Leu
                165
```

(2) INFORMATION FOR SEQ ID NO:31:

(i) SEQUENCE CHARACTERISTICS:
        (A) LENGTH: 166 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:31:

```
Gly Gln Ala Met Ala Lys Arg Val Lys Ala Thr Ile Leu Tyr Ala Thr
1               5                   10                  15

Glu Thr Gly Lys Ser Gln Ala Tyr Ala Lys Thr Leu Cys Glu Ile Phe
            20                  25                  30

Lys His Ala Phe Asp Ala Lys Ala Met Ser Met Glu Glu Tyr Asp Ile
        35                  40                  45
```

-continued

```
Val His Leu Glu His Glu Ala Leu Val Leu Val Val Thr Ser Thr Phe
     50                      55                      60

Gly Asn Gly Asp Pro Pro Glu Asn Gly Glu Lys Phe Gly Cys Ala Leu
 65                  70                  75                  80

Met Glu Met Arg His Pro Asn Ser Val Gln Glu Arg Lys Ser Tyr
                 85                  90                  95

Lys Val Arg Phe Asn Ser Val Ser Ser Tyr Ser Asp Ser Arg Lys Ser
                100                 105                 110

Ser Gly Asp Gly Pro Asp Leu Arg Asp Asn Phe Glu Ser Thr Gly Pro
            115                 120                 125

Leu Ala Asn Val Arg Phe Ser Val Phe Gly Leu Gly Ser Arg Ala Tyr
        130                 135                 140

Pro His Phe Cys Ala Phe Gly His Ala Val Asp Thr Leu Leu Glu Glu
145                 150                 155                 160

Leu Gly Gly Glu Arg Ile
                165
```

(2) INFORMATION FOR SEQ ID NO:32:

(i) SEQUENCE CHARACTERISTICS:
        (A) LENGTH: 123 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:32:

```
Arg Lys Val Met Ala Ser Arg Val Arg Ala Thr Val Leu Phe Ala Thr
  1               5                  10                  15

Glu Thr Gly Lys Ser Glu Ala Leu Ala Arg Asp Leu Ala Thr Leu Phe
                 20                  25                  30

Ser Tyr Ala Phe Asn Thr Lys Val Val Cys Met Asp Gln Tyr Lys Ala
                 35                  40                  45

Ser Thr Leu Glu Glu Glu Gln Leu Leu Leu Val Val Thr Thr Phe Gly
     50                      55                      60

Asn Gly Asp Cys Pro Ser Asn Gly Gln Thr Leu Lys Lys Ser Leu Phe
 65                  70                  75                  80

Met Leu Arg Glu Leu Asn His Thr Phe Arg Tyr Ala Val Phe Gly Leu
                 85                  90                  95

Gly Ser Ser Met Tyr Pro Gln Phe Cys Ala Phe Ala His Asp Ile Asp
                100                 105                 110

Gln Lys Leu Ser His Leu Gly Ala Ser Gln Leu
            115                 120
```

(2) INFORMATION FOR SEQ ID NO:33:

(i) SEQUENCE CHARACTERISTICS:
        (A) LENGTH: 116 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:33:

```
Ala Ile Thr Gly Ile Phe Phe Gly Ser Asp Thr Gly Asn Thr Glu Asn
  1               5                  10                  15

Ile Ala Lys Met Ile Gln Lys Gln Leu Gly Lys Asp Val Ala Asp Val
```

-continued

```
                  20                  25                  30
His Asp Ile Ala Lys Ser Ser Lys Glu Asp Leu Glu Ala Tyr Asp Ile
            35                  40                  45

Leu Leu Leu Gly Ile Pro Thr Trp Tyr Tyr Gly Glu Ala Gln Cys Asp
    50                  55                  60

Trp Asp Asp Phe Phe Pro Thr Leu Glu Ile Asp Phe Asn Gly Lys
65                  70                  75                  80

Leu Val Ala Leu Phe Gly Cys Gly Asp Gln Glu Asp Tyr Ala Glu Tyr
                85                  90                  95

Phe Cys Asp Ala Leu Gly Thr Ile Arg Asp Ile Ile Glu Pro Arg Gly
                100                 105                 110

Ala Thr Ile Val
        115

(2) INFORMATION FOR SEQ ID NO:34:

(i) SEQUENCE CHARACTERISTICS:
        (A) LENGTH: 120 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:34:

Met Pro Lys Ala Leu Ile Val Tyr Gly Ser Thr Thr Gly Asn Thr Glu
1               5                   10                  15

Tyr Thr Ala Glu Thr Ile Ala Arg Glu Leu Ala Asp Ala Gly Tyr Glu
            20                  25                  30

Val Asp Ser Arg Asp Ala Ala Ser Val Glu Ala Gly Gly Leu Phe Glu
        35                  40                  45

Gly Phe Asp Leu Val Leu Leu Gly Cys Ser Thr Trp Gly Asp Asp Ser
    50                  55                  60

Ile Glu Leu Gln Asp Asp Phe Ile Pro Leu Phe Asp Ser Leu Glu Glu
65                  70                  75                  80

Thr Gly Ala Gln Gly Arg Lys Val Ala Cys Phe Gly Cys Gly Asp Ser
                85                  90                  95

Ser Tyr Glu Tyr Phe Cys Gly Ala Val Asp Ala Ile Glu Glu Lys Leu
                100                 105                 110

Lys Asn Leu Gly Ala Glu Ile Val
        115                 120

(2) INFORMATION FOR SEQ ID NO:35:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:35:

Ala Val Asp Thr Arg Leu Glu Glu Leu Gly Gly Glu Arg Thr
1               5                   10
```